United States Patent
Angus (10) Patent No.: US 10,117,678 B2
(45) Date of Patent: Nov. 6, 2018

(54) SURGICAL SYSTEM FOR BONE SCREW INSERTION AND ROD REDUCTION

(71) Applicant: K2M, Inc., Leesburg, VA (US)

(72) Inventor: Olivia Angus, Arlington, VA (US)

(73) Assignee: K2M, Inc., Leesburg, VA (US)

( * ) Notice: Subject to any disclaimer, the term of this patent is extended or adjusted under 35 U.S.C. 154(b) by 20 days.

(21) Appl. No.: 15/165,423

(22) Filed: May 26, 2016

(65) Prior Publication Data

US 2016/0346011 A1    Dec. 1, 2016

Related U.S. Application Data

(60) Provisional application No. 62/167,367, filed on May 28, 2015.

(51) Int. Cl.
*A61B 17/70* (2006.01)

(52) U.S. Cl.
CPC ...... *A61B 17/7032* (2013.01); *A61B 17/7082* (2013.01); *A61B 17/7086* (2013.01)

(58) Field of Classification Search
USPC .......................................... 606/53–59, 86 B
See application file for complete search history.

(56) References Cited

U.S. PATENT DOCUMENTS

| | | | |
|---|---|---|---|
| 3,604,487 A | 9/1971 | Gilbert | |
| 5,364,397 A | 11/1994 | Hayes et al. | |
| 5,720,751 A | 2/1998 | Jackson | |
| 5,733,286 A | 3/1998 | Errico et al. | |
| 5,910,141 A | 6/1999 | Morrison et al. | |
| 6,440,133 B1 | 8/2002 | Beale et al. | |
| 6,648,888 B1 | 11/2003 | Shluzas | |
| 6,743,231 B1 | 6/2004 | Gray et al. | |
| 6,790,208 B2 | 9/2004 | Oribe et al. | |
| 7,156,849 B2 | 1/2007 | Dunbar et al. | |
| 7,160,300 B2 | 1/2007 | Jackson | |
| 7,179,261 B2 | 2/2007 | Sicvol et al. | |
| 7,226,453 B2 | 6/2007 | Chao et al. | |
| 7,250,052 B2 | 7/2007 | Landry et al. | |
| 7,371,239 B2 | 5/2008 | Dec et al. | |
| 7,462,182 B2 | 12/2008 | Lim | |

(Continued)

FOREIGN PATENT DOCUMENTS

WO    2014062692 A1    4/2014

OTHER PUBLICATIONS

European Search Report EP16171675.8 dated Oct. 21, 2016.

*Primary Examiner* — Eduardo C Robert
*Assistant Examiner* — Tara R Carter
(74) *Attorney, Agent, or Firm* — Carter, DeLuca, Farrell & Schmidt, LLP (57) ABSTRACT

A screw insertion instrument includes a housing, a knob, a drive shaft, and a screw alignment post. The housing includes a proximal portion and a distal portion, and the proximal portion includes a proximal body portion defining a channel extending longitudinally therethrough along a longitudinal axis of the housing. The knob is coupled to the proximal portion of the housing and defines an aperture therethrough that is aligned with the longitudinal axis of the housing. The drive shaft extends through the aperture of the knob and the proximal portion of the housing. The screw alignment post is coupled to the distal portion of the housing and is aligned with the longitudinal axis of the housing.

12 Claims, 5 Drawing Sheets

(56) References Cited

U.S. PATENT DOCUMENTS

| | | |
|---|---|---|
| 7,491,207 B2 | 2/2009 | Keyer et al. |
| 7,520,879 B2 | 4/2009 | Justis et al. |
| 7,572,264 B2 | 8/2009 | Null et al. |
| 7,608,081 B2 | 10/2009 | Abdelgany |
| 7,618,442 B2 | 11/2009 | Spitler et al. |
| 7,621,918 B2 | 11/2009 | Jackson |
| 7,651,502 B2 | 1/2010 | Jackson |
| 7,666,189 B2 | 2/2010 | Gerber et al. |
| 7,887,541 B2 | 2/2011 | Runco et al. |
| 7,922,749 B2 | 4/2011 | Dewey |
| 7,927,334 B2 | 4/2011 | Miller et al. |
| 7,988,694 B2 | 8/2011 | Barrus et al. |
| 8,162,991 B2 | 4/2012 | Strauss et al. |
| 8,303,595 B2 | 11/2012 | Jones |
| 8,308,729 B2 | 11/2012 | Nunley et al. |
| 8,764,756 B2 | 7/2014 | Jones |
| 8,882,817 B2 | 11/2014 | Jones et al. |
| 8,961,523 B2 | 2/2015 | Barrus et al. |
| 2003/0040746 A1* | 2/2003 | Mitchell ............ A61B 17/1606 623/17.11 |
| 2003/0225408 A1 | 12/2003 | Nichols et al. |
| 2004/0267275 A1 | 12/2004 | Cournoyer et al. |
| 2005/0059969 A1 | 3/2005 | McKinley |
| 2005/0149053 A1 | 7/2005 | Varieur et al. |
| 2005/0192589 A1 | 9/2005 | Raymond et al. |
| 2005/0228400 A1 | 10/2005 | Chao et al. |
| 2006/0036260 A1 | 2/2006 | Runco et al. |
| 2006/0089651 A1 | 4/2006 | Trudeau et al. |
| 2006/0200132 A1 | 9/2006 | Chao et al. |
| 2006/0264962 A1* | 11/2006 | Chin ................ A61B 17/7037 606/90 |
| 2007/0213722 A1 | 9/2007 | Jones et al. |
| 2007/0270867 A1 | 11/2007 | Miller et al. |
| 2007/0276379 A1 | 11/2007 | Miller et al. |
| 2008/0015601 A1* | 1/2008 | Castro ................ A61B 17/7086 606/86 R |
| 2008/0172062 A1 | 7/2008 | Donahue et al. |
| 2009/0018593 A1* | 1/2009 | Barrus ............... A61B 17/7086 606/86 A |
| 2009/0105716 A1 | 4/2009 | Barrus |
| 2009/0105769 A1 | 4/2009 | Rock et al. |
| 2010/0262198 A1 | 10/2010 | Braunschweiler et al. |
| 2011/0087298 A1 | 4/2011 | Jones |
| 2011/0118791 A1 | 5/2011 | Nunley et al. |
| 2011/0172714 A1 | 7/2011 | Boachie-Adjei et al. |
| 2013/0184763 A1 | 7/2013 | McClintock et al. |
| 2014/0163625 A1* | 6/2014 | Meyer ............... A61B 17/7086 606/86 A |
| 2015/0100097 A1 | 4/2015 | Barrus |
| 2015/0100098 A1 | 4/2015 | Moore |

* cited by examiner

SURGICAL SYSTEM FOR BONE SCREW INSERTION AND ROD REDUCTION

CROSS-REFERENCE TO RELATED APPLICATIONS

This application claims the benefit of, and priority to, U.S. Provisional Patent Application Ser. No. 62/167,367, filed on May 28, 2015, the entire contents of which are hereby incorporated herein by reference.

TECHNICAL FIELD

The present disclosure relates generally to a surgical instrument for securing a spinal fixation device during an orthopedic spine surgery procedure, and more particularly, to a surgical system and method for inserting a bone screw into a vertebral body and reducing a spinal rod into the bone screw.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages, and cadaver and human bone implants. In order to facilitate stabilizing the spine and keeping the interbody implant in position, other spinal fixation apparatuses are commonly employed, such as bone screws and spinal rods to connect the interbody implant with the cranial and caudal vertebrae. In complex spine cases, such as scoliosis, and minimally invasive surgical procedures, it is often challenging to insert bone screws and align them with a spinal rod.

Therefore, a need exists for a system that easily and reliably implants a bone screw and captures a spinal rod for complete reduction of the spinal rod into a saddle of the bone screw.

SUMMARY

The present disclosure is direct to a system including a screw insertion instrument that captures a bone screw and/or a rod reduction device to facilitate ease of insertion of the bone screw into a vertebral body and/or a spinal rod into a saddle of the bone screw.

In accordance with an aspect of the present disclosure, a screw insertion instrument includes a housing, a knob, a drive shaft, and a screw alignment post. The housing includes a proximal portion and a distal portion, and the proximal portion includes a proximal body portion defining a channel extending longitudinally therethrough along a longitudinal axis of the housing. The knob is coupled to the proximal portion of the housing and defines an aperture therethrough that is aligned with the longitudinal axis of the housing. The drive shaft extends through the aperture of the knob and the proximal portion of the housing. The screw alignment post is coupled to the distal portion of the housing and is aligned with the longitudinal axis of the housing.

In embodiments, the housing includes an intermediate portion disposed distally of the proximal portion. The intermediate portion includes a recess defined therein that is aligned and in communication with the channel of the proximal portion. The housing may further include a connecting portion interconnecting the intermediate portion with the distal portion. The connecting portion may be radially offset from the longitudinal axis of the housing.

The distal portion of the housing may include a distal body portion and first and second arms extending distally therefrom. A proximal end portion of the screw alignment post may be secured to the distal body portion and an elongated body of the screw alignment post may extend distally between the first and second arms.

In embodiments, the screw insertion instrument includes a handle disposed between the housing and the knob. The handle defines a channel extending longitudinally therethrough that is aligned with the longitudinal axis of the housing. The handle may include a body portion disposed over the proximal portion of the housing and a head portion disposed within a cavity defined in a distal end of the knob.

The proximal portion of the housing may include a threaded outer surface threadingly engaged with a threaded inner surface of the aperture of the knob. A proximal portion of the drive shaft may be secured within the aperture of the knob, and a distal portion of the drive shaft may be secured to the proximal portion of the housing.

In accordance with another aspect of the present disclosure, a system for securing spinal fixation devices includes a screw insertion instrument and a rod reduction device. The screw insertion instrument includes a housing, a knob, a drive shaft, and a screw alignment post. The housing includes a proximal portion and a distal portion, and the proximal portion includes a proximal body portion defining a channel extending longitudinally therethrough along a longitudinal axis of the housing. The knob is coupled to the proximal portion of the housing and defines an aperture therethrough that is aligned with the longitudinal axis of the housing. The drive shaft extends through the aperture of the knob and the proximal portion of the housing. The screw alignment post is coupled to the distal portion of the housing and is aligned with the longitudinal axis of the housing. The rod reduction device is removably received within the housing of the screw insertion instrument.

In embodiments, a tail portion of the drive shaft of the screw insertion instrument is releasably engaged with a head portion of a shaft of the rod reduction device. A proximal portion of the drive shaft may be secured within the aperture of the knob, and the knob may be movable between an engaged position and a released position to move the drive shaft longitudinally. The drive shaft may be movable distally when the knob is moved from the released position to the engaged position and proximally when the knob is moved from the engaged position to the released position. A distal portion of the drive shaft may be secured to the proximal portion of the housing such that, when the knob is in the engaged position, rotation of the drive shaft results in rotation of the housing and the rod reduction device.

The system may include a bone screw, and the screw alignment post may include a distal end portion releasably engaged with the bone screw.

In embodiments, the housing includes an intermediate portion disposed distally of the proximal portion. The intermediate portion includes a recess defined therein that is aligned and in communication with the channel of the proximal portion. A shaft of the rod reduction device is disposed within the recess of the intermediate portion and extends along the longitudinal axis of the housing.

The housing may include a connecting portion interconnecting the intermediate portion with the distal portion. The connecting portion may be radially offset from the longitudinal axis of the housing. A housing and an anvil of the rod reduction device may be disposed between the intermediate and distal portions of the housing of the screw insertion instrument.

The distal portion of the housing may include a distal body portion and first and second arms extending distally therefrom. Arm members of the rod reduction device may extend around the distal body portion and be offset about 90° with respect to the first and second arms of the housing.

In accordance with yet another aspect of the present disclosure, a method of securing spinal fixation devices includes attaching a bone screw to a screw alignment post of a screw insertion instrument and fastening the bone screw to a bony structure. The screw insertion instrument includes a housing, a knob, a drive shaft, and the screw alignment post. The housing includes a proximal portion and a distal portion, and the proximal portion includes a proximal body portion defining a channel extending longitudinally therethrough along a longitudinal axis of the housing. The knob is coupled to the proximal portion of the housing and defines an aperture therethrough that is aligned with the longitudinal axis of the housing. The drive shaft extends through the aperture of the knob and the proximal portion of the housing. The screw alignment post is coupled to the distal portion of the housing and is aligned with the longitudinal axis of the housing.

In embodiments, the method includes securing a rod reduction device within the housing of the screw insertion instrument and attaching the rod reduction device to the bone screw prior to fastening the bone screw. Securing the rod reduction device may include rotating the knob of the screw insertion instrument to an engaged position to move the drive shaft distally such that a tail portion of the drive shaft engages a head portion of a shaft of the rod reduction device.

In embodiments, the method further includes removing the screw insertion instrument from the rod reduction device after fastening the bone screw, leaving the rod reduction device attached to the bone screw. Removing the screw insertion instrument may include rotating the knob of the screw insertion instrument to a released position to move the drive shaft proximally such that a tail portion of the drive shaft disengages a head portion of a shaft of the rod reduction device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the present disclosure are now described in detail with reference to the drawings in which like reference numerals designate identical or corresponding elements in each of the several views. In this disclosure, the term "clinician" refers to a doctor (e.g., a surgeon), a nurse, or any other care provider, and may include support personnel. As used herein, the term "proximal" refers to a portion of a system, device, or component thereof that is closer to a clinician, and the term "distal" will refer to the portion of the system, device, or component thereof that is farther from the clinician. "Cranial" refers to a spine segment closer to the head of a patient, whereas "caudal" refers to the spine segment closer to the feet of the patient. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring initially to FIGS. 1-4, a screw insertion instrument 10 includes a housing 20, a screw alignment post 30 extending distally from the housing 20, a handle 40, a knob 50, and a drive shaft 60 extending proximally from the housing 20. The screw insertion instrument 10 defines a longitudinal axis "X" through a center thereof. The screw insertion instrument 10 is configured to releasably engage and drive a bone screw 100 (FIG. 10) into a bony structure of a spine (e.g., a pedicle or facet of a vertebral body), and to releasably couple with a rod reduction device 200 (FIG. 10) for reducing a spinal rod 300 (FIG. 11) into the bone screw 100.

Figure 4:
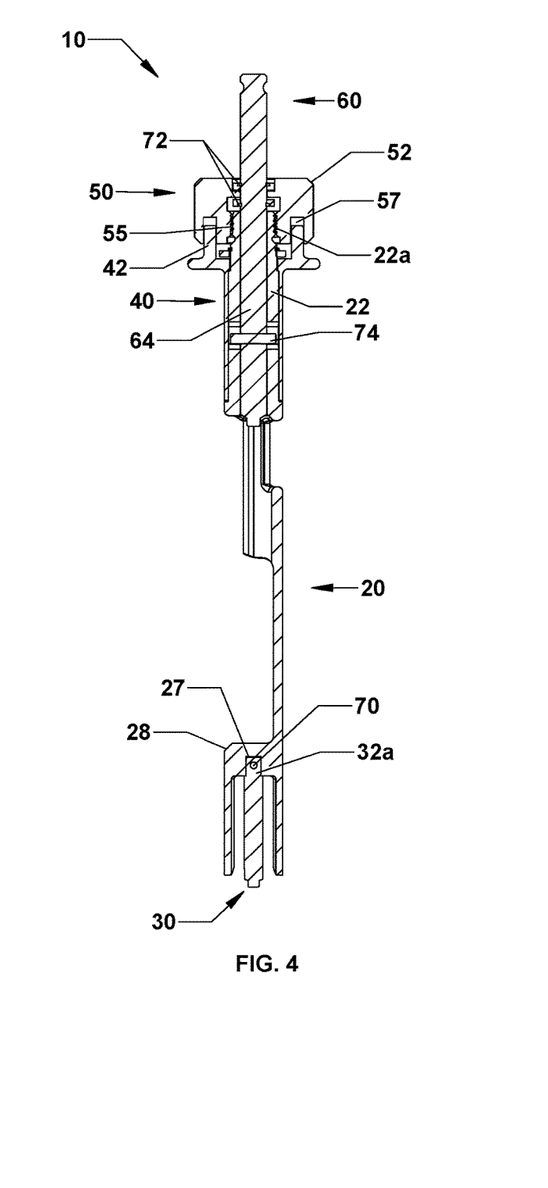
FIG. 4 is a side cross-sectional view of the screw insertion instrument of FIGS. 1-3, taken along line 4-4 of FIG. 3.
Figure 5:
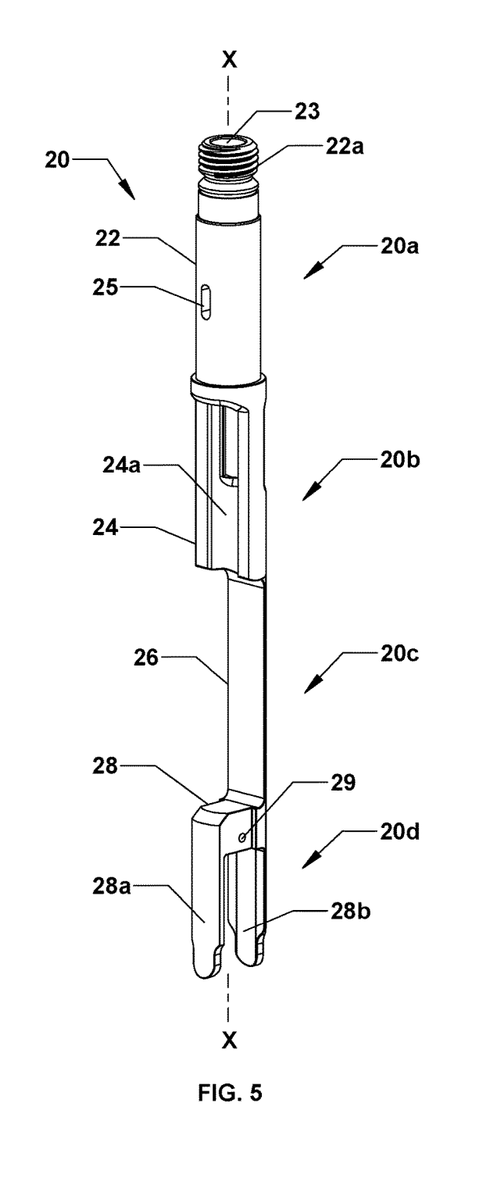
FIG. 5 is a perspective view of a housing of the screw insertion instrument of FIGS. 1-4.

As shown in FIG. 5, in conjunction with FIGS. 1-4, the housing 20 of the screw insertion instrument 10 is a unitary structure including, from proximal end to distal end, a proximal portion 20a, an intermediate portion 20b, a connecting portion 20c, and a distal portion 20d. The proximal portion 20a includes a proximal body portion 22 that is substantially cylindrical and defines a channel 23 extending longitudinally therethrough along longitudinal axis "X." The proximal body portion 22 is configured to support the handle 40 (see e.g., FIG. 4) thereon, and includes an outer threaded surface 22a disposed at a proximal-most end of the housing 20 that is configured to mate with the knob 50 (see e.g., FIG. 4). The proximal body portion 22 also defines a proximal through hole 25 extending therethrough along an axis transverse to the longitudinal axis "X" and is disposed distally of the outer threaded surface 22a.

The intermediate portion 20b of the housing 20 includes an intermediate body portion 24 defining a recess 24a in an inner surface thereof that is aligned and in communication with the channel 23 of the proximal portion 20a of the housing 20. The connecting portion 20c includes an elongated connecting member 26, such as a rod or bar, interconnecting the proximal and intermediate portions 20a, 20b with the distal portion 20d. The elongated connecting member 26 is radially offset from the longitudinal axis "X."

Figure 10:
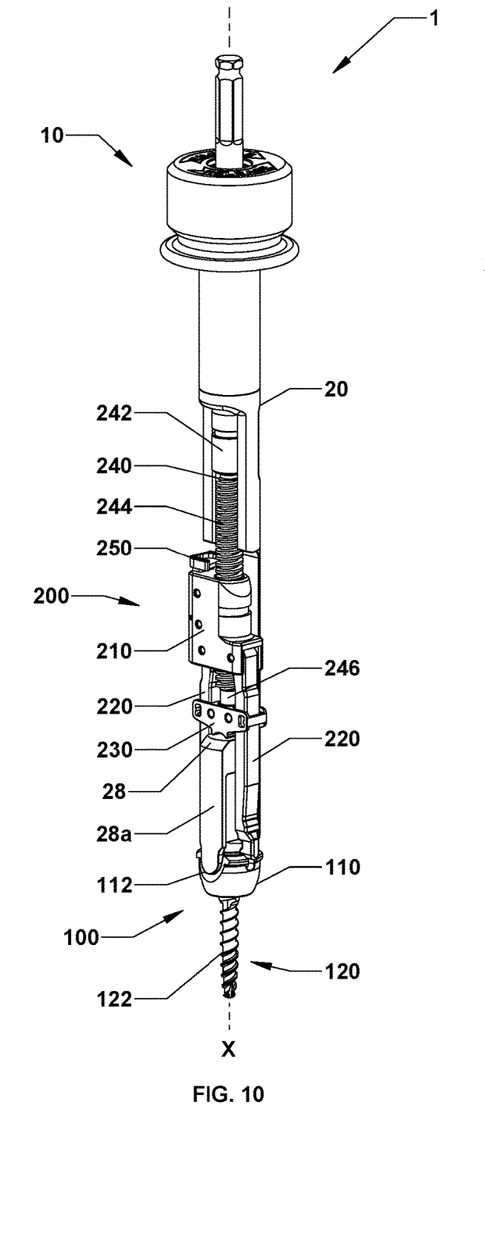
FIG. 10 is a perspective view of a system including the screw insertion instrument of FIGS. 1-4 coupled to a bone screw and a rod reduction device in accordance with an embodiment of the present disclosure.

The distal portion 20d includes a distal body portion 28 having first and second arms 28a, 28b extending distally therefrom in opposed relation to each other. The first and second arms 28a, 28b are radially offset from the longitudinal axis "X" and are configured to align with and/or engage an outer portion of a bone screw 100 (FIG. 10). The distal body portion 28 includes a cavity 27 (FIG. 4) defined in a distal surface thereof that is configured to receive a portion of the screw alignment post 30. The distal body portion 28 also defines a distal through hole 29 extending therethrough along an axis transverse to the longitudinal axis "X."

Figure 6:
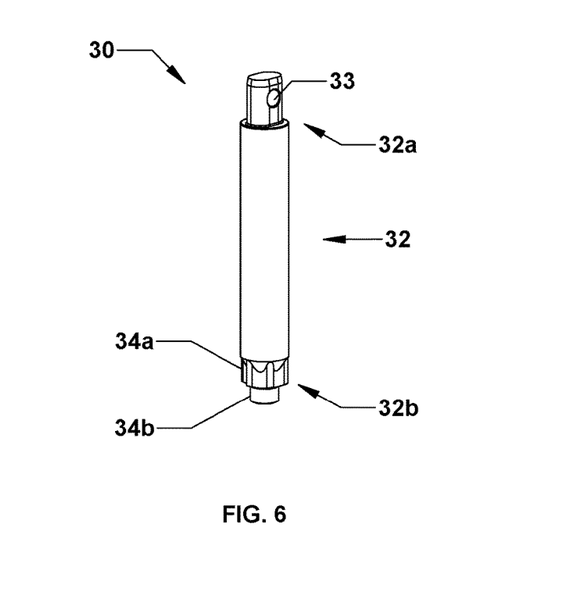
FIG. 6 is a perspective view of a screw alignment post of the screw insertion instrument of FIGS. 1-4.

As shown in FIGS. 4 and 6, a screw alignment post 30 includes an elongated body 32 including a proximal end portion 32a and a distal end portion 32b. The proximal end portion 32a includes a through hole 33 defined therethrough that is configured to align with the distal through hole 29 of the distal portion 20d of the housing 20. In embodiments, the proximal end portion 32a may have a shaped outer surface that is complementary in geometry with the cavity 27 of the distal body portion 28 of the housing 20 to aid in aligning the through hole 33 of the screw alignment post 30 with the distal through hole 29 of the distal portion 20d of the housing 20. The proximal end portion 32a of the screw alignment post 30 is received within the distal body portion 28 of the housing 20, and is secured thereto via a distal pin 70 (FIGS. 1 and 4) positioned through the distal through hole 29 of the housing 20 and the through hole 33 of the screw alignment post 30.

With continued reference to FIGS. 4 and 6, the elongated body 32 of the screw alignment post 30 extends distally between the first and second arms 28a and 28b of the distal portion 20d of the housing 20 and along the longitudinal axis "X" for aligning a bone screw 100 (FIG. 10) with the housing 20. The distal end portion 32b of the screw alignment post 30 includes a hex shaped region 34a and a distal protrusion 34b extending distally from the hex shaped region 34a that are configured to engage a portion of the bone screw 100 (FIG. 10). It should be understood, however, that the screw alignment post 30, and portions thereof, may assume other shapes and configurations depending upon the bone screw(s) utilized with the screw insertion instrument 10 as is within the purview of those skilled in the art. For example, in some embodiments, the screw alignment post 30 may be spring-loaded or adjustable to accommodate various bone screw types and sizes.

Figure 7:
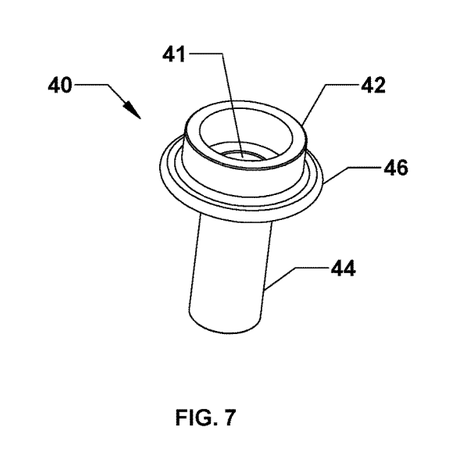
FIG. 7 is a perspective view of a handle of the screw insertion instrument of FIGS. 1-4.

Referring now to FIGS. 4 and 7, the handle 40 includes a head portion 42, a body portion 44 extending distally from the head portion 42, and a flange 46 extending radially outwardly from the head portion 42 at a transition area with the body portion 44. The handle 40 defines a channel 41 extending longitudinally therethrough along longitudinal axis "X." The body portion 44 is sized to receive the proximal portion 20a of the housing 20 therein (see e.g., FIG. 4).

Figure 8:
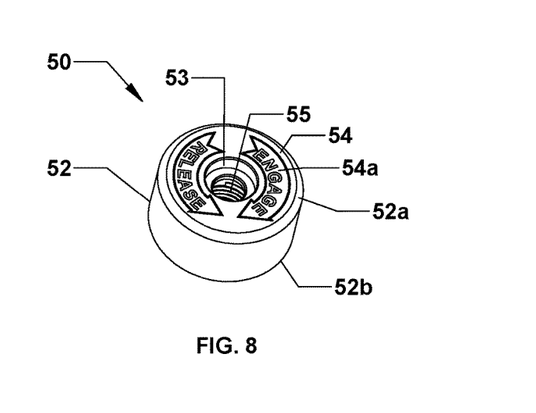
FIG. 8 is a top perspective view of a knob of the screw insertion instrument of FIGS. 1-4.

As shown in FIGS. 4 and 8, the knob 50 includes a knob body 52 including an aperture 53 extending therethrough from proximal end 52a to a distal end 52b of the knob body 52. A distal portion of the aperture 53 defines a threaded inner surface 55. The proximal end 52a includes a proximal surface 54 on which indicia 54a, such as instructional information, may be disposed. The distal end 52b defines a cavity 57 (FIG. 4) therein that is configured to receive the head portion 42 of the handle 40 therein, and the threaded inner surface 55 of the aperture 53 is configured to threadingly engage the outer threaded surface 22a of the proximal portion of the housing 20 to secure the knob 50 and the handle 40 thereto. It should be understood that other mechanical engagement mechanisms may be utilized between the knob 50 and the housing 20, as is within the purview of those skilled in the art. For example, the knob 50 and the housing 20 may include a ratchet mechanism and/or the knob 50 may assume locked and unlocked positions with respect to the housing 20.

Figure 9:
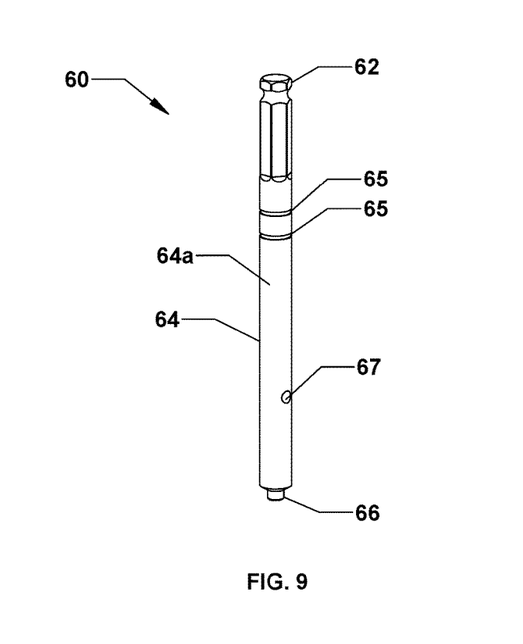
FIG. 9 is a perspective view of a drive shaft of the screw insertion instrument of FIGS. 1-4.

Referring now to FIGS. 4 and 9, the drive shaft 60 includes a head portion 62, an elongated body 64, and a tail portion 66. The head portion 62 is configured to mate with a variety of instruments, such as manual or powered drive handles and/or devices. In embodiments, the head portion 62 is a hex head, however, it should be understood that the head portion 62 may assume other shapes and configuration depending upon the instrument utilized to drive the drive shaft 60 as is within the purview of those skilled in the art. The elongate body 64 includes a plurality of grooves 65 defined in an outer surface 64a thereof that are configured to engage a plurality of retaining ring and washer assemblies 72 (FIGS. 1 and 4) disposed within the knob body 52 of the knob 50 to aid in alignment of the drive shaft 60 inside the handle 40, to minimize and/or prevent sliding of the drive shaft 60 relative to the knob 50, and to absorb and/or distribute forces acted upon the drive shaft 60. The elongate body 64 also defines a through hole 67 therethrough, distal of the plurality of grooves 65, that is configured to align with the proximal through hole 25 of the proximal portion 20a of the housing 20.

Figure 1:
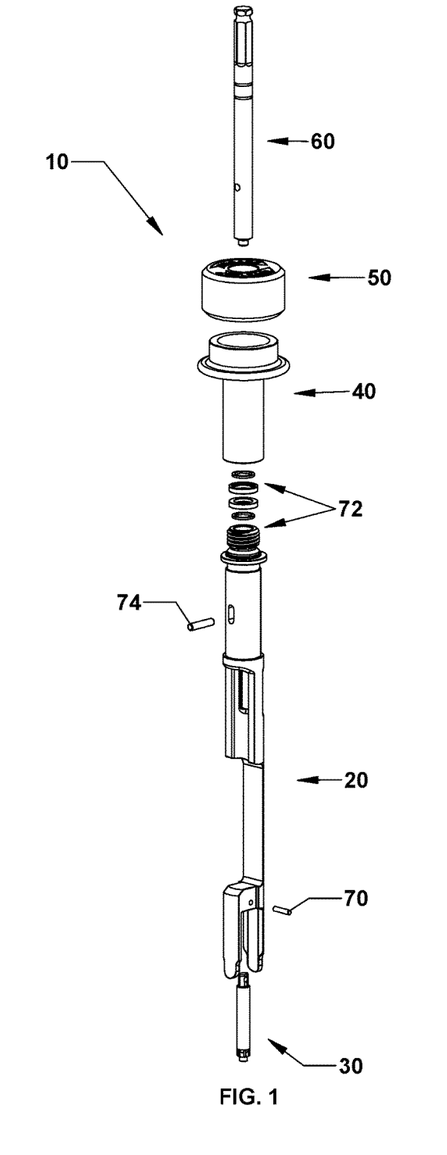
FIG. 1 is an exploded view, with parts separated, of a screw insertion instrument in accordance with an embodiment of the present disclosure.
Figure 2:
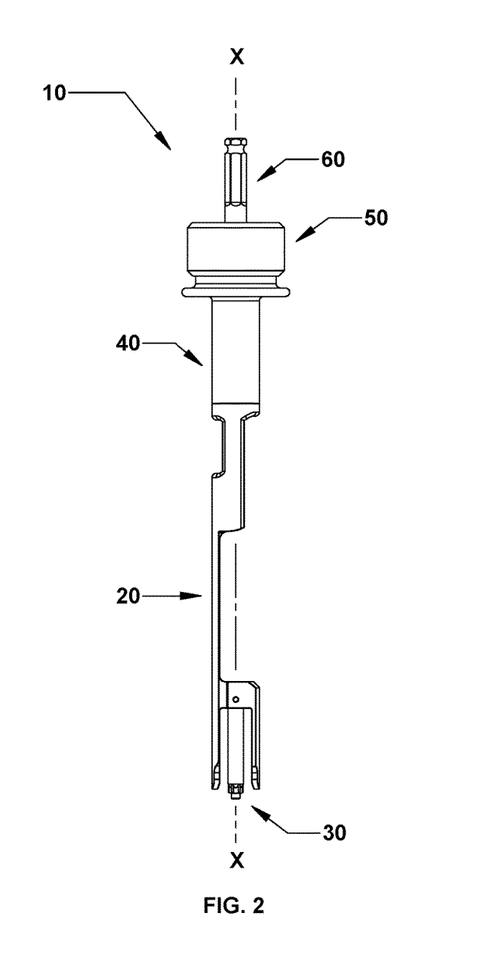
FIG. 2 is side view of the assembled screw insertion instrument of FIG. 1.
Figure 3:
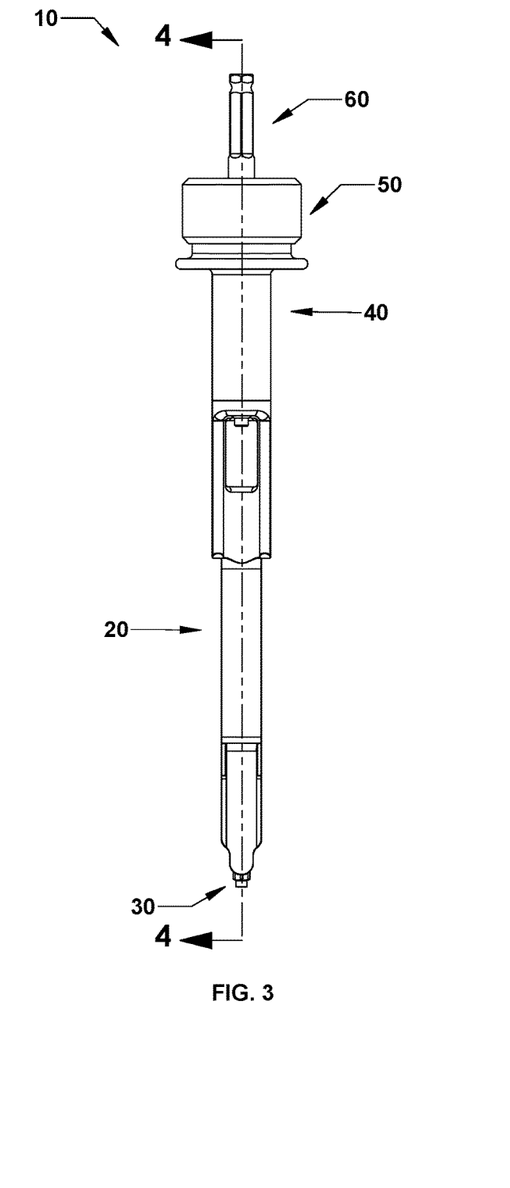
FIG. 3 is a front view of the screw insertion instrument of FIGS. 1 and 2.

With specific reference to FIGS. 1, 4, and 9, the elongate body 64 of the drive shaft 60 is received within the proximal portion 20a of the housing 20 and is secured thereto via a proximal pin 74 positioned through the proximal through hole 25 (FIG. 5) of the housing 20 and the through hole 67 of the drive shaft 60. The mechanical engagement between the drive shaft 60 and the housing 20 restricts the longitudinal distance in which the knob 50 moves the housing 20 proximally or distally along the drive shaft 60, and the knob 50 controls the depth in which the drive shaft 60 moves relative to the handle 40.

With continued reference to FIGS. 4 and 9, the tail portion 66 of the drive shaft 60 is a distal protrusion shaped and sized to engage a proximal end of a rod reduction device 200 (FIG. 10). It should be understood, however, that the tail portion 66 of the drive shaft 60 may assume other shapes and/or sizes that are configured to engage a rod reduction device 200, as is within the purview of those skilled in the art.

Referring now to FIG. 10, the screw insertion instrument 10 is configured for use with a bone screw 100 and a rod reduction device 200. Suitable bone screws include, for example, polyaxial pedicle screws such as those shown in U.S. Pat. No. 8,882,817, taper lock screws such as those shown in U.S. Pat. Nos. 7,988,694 and 8,162,991, set screw systems such as those shown in U.S. Pat. No. 5,733,286, mono-axial screws such as those shown in U.S. Patent Appl. Pub. No. 2009/0105716, and uniplanar screws such as those shown in U.S. Patent Appl. Pub. No. 2009/0105769, the entire contents of each of which are hereby incorporated by reference herein. Additionally, suitable rod reduction devices include, for example, those shown in U.S. Pat. Nos. 8,303,595, 8,961,523, and 8,308,729, the entire contents of each of which are hereby incorporated by reference herein.

The bone screw 100 and the rod reduction device 200 will only further be described to the extent necessary to fully disclose the aspects of the present disclosure. For detailed description of an exemplary bone screw and rod reduction device, reference may be made to U.S. Patent Appl. Pub. No. 2015/0100097, the entire contents of which are hereby incorporated by reference herein.

Figure 11:
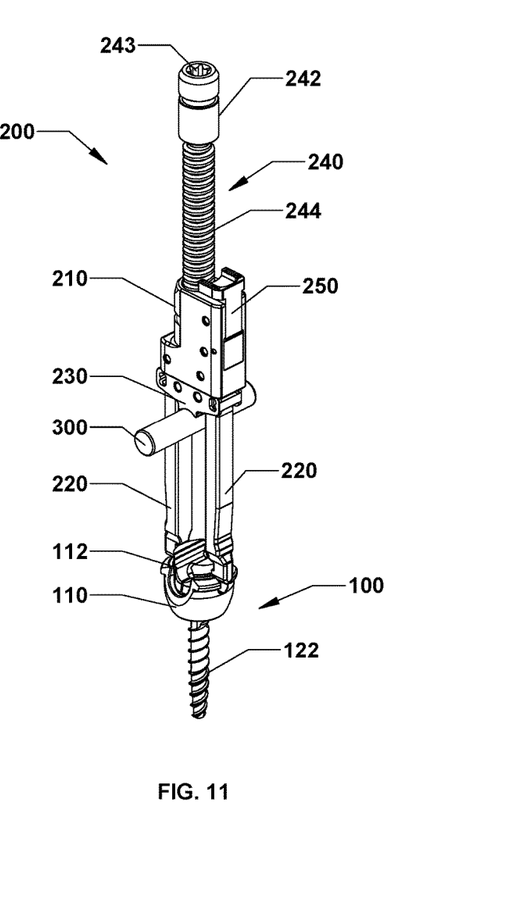
FIG. 11 is a perspective view of the bone screw and the rod reduction device of the system of FIG. 10, and further including a spinal rod in accordance with an embodiment of the present disclosure.

As shown in FIGS. 10 and 11, the bone screw 100 includes a housing 110 and a screw member 120. The housing 110 defines a saddle 112 therein, and the screw member 120 includes a head (not shown) disposed within the housing 110 and a threaded shaft 122 extending from the head distally through the housing 110.

The rod reduction device 200 includes a housing 210, arm members 220, an anvil 230, a shaft 240, and a button 250. The arm members 220 extend distally from the housing 210 and are configured to engage the housing 110 of the bone screw 100. The anvil 230 is coupled to the shaft 240 and disposed around the arm members 220 such that proximal and distal translation of the anvil 230 causes each arm member 220 to pivot with respect to the housing 210. The shaft 240 includes a head portion 242 having a proximal recess 243 defined therein, an elongated threaded body 244 extending distally from the head portion 242, and a distal end portion 246 secured to the anvil 230. The button 250 is slidably disposed in the housing 210 and configured to rotate and/or linearly move the shaft 240 relative to the housing 210.

In an embodiment, a system 1 is assembled as shown in FIG. 10. The rod reduction device 200 is releasably attached to the screw insertion instrument 10. The shaft 240 of the rod reduction device 200 is inserted into the housing 20 of the screw insertion instrument 10 such that the shaft 240 extends along the longitudinal axis "X" of the screw insertion instrument 10, with a portion of the shaft 240 is disposed within the recess 24a of the intermediate portion 20b of the housing 20. The anvil 230 of the rod reduction device 200 is disposed between the housing 210 of the rod reduction device 200 and the distal body portion 28 of the housing 20 of the screw insertion instrument 10, and is longitudinally movable therebetween by rotating the head portion 242 of the shaft 240 to adjust the fit of the anvil 230 within the housing 20 of the screw insertion instrument 10. The arm members 220 of the rod reduction device 200 extend around the distal body portion 28 of the housing 20 of the screw insertion instrument 10 and are offset by about 90° with respect to the first and second arms 28a and 28b of the housing 20. The knob 50 of the screw insertion instrument 10 is rotatable (e.g., clockwise) to an engaged position to move the knob 50 and thus, the drive shaft 60 and the housing 20 distally such that the tail portion 66 (see e.g., FIG. 9) of the drive shaft 60 engages the recess 243 (FIG. 11) defined in the head portion 242 of the shaft 240 to lock or hold the rod reduction device 200 firmly within the housing 20 of the screw insertion instrument 10. The bone screw 100 is aligned with the screw alignment post 30 of the screw insertion instrument 10 and attached to the distal end portion 32b of the screw alignment post 30. Distal ends of the arm members 220 of the rod reduction device 200 are attached to the housing 110 of the bone screw 100.

In use, a clinician may perform various discectomy or disc procedures to prepare a disc space and then, if the clinician needs to attach posterior instrumentation, the clinician attaches a driver instrument (e.g., a manual or powered drive handle and/or device) to the head portion 62 of the drive shaft 60 of the screw insertion instrument 10 which has been assembled with the rod reduction device 200 as described above, to drive the bone screw 100 into a bony structure, e.g., a vertebral body. With the head portion 62 of the drive shaft 60 secured to the driver instrument (not shown), the elongated body 64 of the drive shaft 60 secured to the housing 20 of the screw insertion instrument 10, and the tail portion 66 of the drive shaft 60 secured to the rod reduction device 200, actuation of the driver instrument (not shown) results in rotation of the assembled system 1 to drive the threaded shaft 122 of the bone screw 100 into the bony structure. Once the bone screw 100 is fully inserted and properly positioned within the bony structure, the screw insertion instrument 10 is removed by turning the knob 50 (e.g., counter clockwise) to a released position to move the knob 50, the drive shaft 60, and the housing 20 proximally to release the tail portion 66 of the drive shaft 60 from the head portion 242 of the shaft 240 of the rod reduction device 200. The screw insertion instrument 10 may then be separated from the rod reduction device 200.

As shown in FIG. 11, the rod reduction device 200 is left attached to the bone screw 100, and a spinal rod 300 is inserted between the anvil 230 of the rod reduction device 200 and the housing 110 of the bone screw 100. Any compression or distraction maneuvers may be performed, and the rod reduction device 200 is then used to push the spinal rod 200 fully into the saddle 112 of the housing 110 of the bone screw 100 by either turning the head portion 242 of the shaft 240 or actuating the button 250 of the housing 210 to lower the anvil 230 towards the bone screw 100. Once the spinal rod 300 is fully reduced, the bone screw 100 may be partially or fully locked to the spinal rod 300 (e.g., a locking instrument may be used to lock the spinal rod in the saddle of the bone screw), and the rod reduction device 200 is removed.

In embodiments, the system 1 may be provided in a kit. The kit is an assembled package including a screw insertion instrument 10, a rod reduction device 200, and optionally, a plurality of bone screws 100 and a plurality of spinal rods 300. The screw insertion instrument 10 may be provided with a variety of alignment posts 30 and/or drive shafts 60 having, for example, different lengths, proximal and/or distal profiles, etc. to accommodate the use of the screw insertion instrument 10 with a variety of bone screws, rod reduction devices, and driver instruments. The plurality of bone screws 100 and plurality of spinal rods 300 may also include a number of different diameter, shapes, and/or lengths. Accordingly, a clinician may pick and choose the components necessary to assemble a screw insertion instrument for use with a rod reduction device, as well as bone screw(s) and spinal rod(s) desired for a surgical procedure.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A screw insertion instrument comprising:
   a housing including a proximal portion and a distal portion, the proximal portion including a proximal body portion defining a channel extending longitudinally therethrough along a longitudinal axis of the housing, the distal portion including first and second arms;
   a knob coupled to the proximal portion of the housing, the knob defining an aperture therethrough that is aligned with the longitudinal axis of the housing;
   a drive shaft extending through the aperture of the knob and the proximal portion of the housing, the drive shaft including a proximal portion secured within the aperture of the knob and a distal portion secured to the proximal portion of the housing via a proximal pin positioned through a proximal through hole of the housing and a through hole of the drive shaft, the knob rotatable between an engaged position and a released position to move the drive shaft longitudinally, the drive shaft movable distally when the knob is rotated from the released position to the engaged position and movable proximally when the knob is rotated from the engaged position to the released position; and
   a screw alignment post coupled to the distal portion of the housing, the screw alignment post positioned between the first and second arms of the distal portion and coincident with the longitudinal axis of the housing.

2. The screw insertion instrument according to claim 1, wherein the housing includes an intermediate portion disposed distally of the proximal portion, the intermediate portion including a recess defined therein that is aligned and in communication with the channel of the proximal portion.

3. The screw insertion instrument according to claim 2, wherein the housing includes a connecting portion interconnecting the intermediate portion with the distal portion, the connecting portion being radially offset from the longitudinal axis of the housing.

4. The screw insertion instrument according to claim 1, wherein the distal portion of the housing includes a distal body portion and the first and second arms extend distally therefrom, and wherein a proximal end portion of the screw alignment post is secured to the distal body portion and an elongated body of the screw alignment post extends distally beyond distal ends of the first and second arms.

5. The screw insertion instrument according to claim 1, further including a handle disposed between the housing and the knob, the handle defining a channel extending longitudinally therethrough that is aligned with the longitudinal axis of the housing, the handle including a body portion disposed over the proximal portion of the housing and a head portion disposed within a cavity defined in a distal end of the knob.

6. The screw insertion instrument according to claim 1, wherein the proximal portion of the housing includes a threaded outer surface threadingly engaged with a threaded inner surface of the aperture of the knob.

7. A system for securing spinal fixation devices, the system comprising:
   a screw insertion instrument including:
      a housing including a proximal portion and a distal portion, the proximal portion including a proximal body portion defining a channel extending longitudinally therethrough along a longitudinal axis of the housing, the distal portion including first and second arms;
      a knob coupled to the proximal portion of the housing, the knob defining an aperture therethrough that is aligned with the longitudinal axis of the housing;
      a drive shaft extending through the aperture of the knob and the proximal portion of the housing, the drive shaft including a proximal portion secured within the aperture of the knob and a distal portion secured to the proximal portion of the housing via a proximal pin positioned through a proximal through hole of the housing and a through hole of the drive shaft, the knob rotatable between an engaged position and a released position to move the drive shaft longitudinally, the drive shaft movable distally when the knob is rotated from the released position to the engaged position and movable proximally when the knob is rotated from the engaged position to the released position; and
      a screw alignment post coupled to the distal portion of the housing, the screw alignment post positioned between the first and second arms of the distal portion and coincident with the longitudinal axis of the housing; and
   a rod reduction device removably received within the housing of the screw insertion instrument.

8. The system according to claim 7, wherein a tail portion of the drive shaft of the screw insertion instrument is releasably engaged with a head portion of a shaft of the rod reduction device.

9. The system according to claim 7, further including a bone screw, and wherein the screw alignment post includes a distal end portion configured to releasably engage a head of the bone screw.

10. The system according to claim 7, wherein the housing includes an intermediate portion disposed distally of the proximal portion, the intermediate portion including a recess defined therein that is aligned and in communication with the channel of the proximal portion, and wherein a shaft of the rod reduction device is disposed within the recess of the intermediate portion and extends along the longitudinal axis of the housing.

11. The system according to claim 10, wherein the housing includes a connecting portion interconnecting the intermediate portion with the distal portion, the connecting portion being radially offset from the longitudinal axis of the housing, and wherein a housing and an anvil of the rod reduction device is disposed between the intermediate and distal portions of the housing of the screw insertion instrument.

12. The system according to claim 7, wherein the distal portion of the housing includes a distal body portion and the first and second arms extend distally therefrom, and wherein arm members of the rod reduction device extend around the distal body portion and are offset about 90° with respect to the first and second arms of the housing.

\* \* \* \* \*